United States Patent [19]

Löbmann et al.

[11] 4,318,903
[45] Mar. 9, 1982

[54] LIVE INFLUENZA VIRUS VACCINE AND THE PREPARATION THEREOF

[75] Inventors: Michèle Löbmann, Cerous-Mousty; Gérard Florent, Genval, both of Belgium

[73] Assignee: Smithkline-Rit, Belgium

[21] Appl. No.: 923,846

[22] Filed: Jul. 12, 1978

[51] Int. Cl.³ .................. A61K 39/12; C12N 7/00; C12N 7/04

[52] U.S. Cl. ..................... 424/89; 435/235; 435/236

[58] Field of Search ............ 424/89; 195/1.1, 1.3; 435/235, 236

[56] References Cited

U.S. PATENT DOCUMENTS

| | | | |
|---|---|---|---|
| 3,953,592 | 4/1976 | Peetermans | 424/89 |
| 3,962,423 | 6/1976 | Peetermans | 195/1.3 |
| 3,991,179 | 11/1978 | Beare | 195/1.3 |
| 4,009,258 | 2/1977 | Kilbourne | 424/89 |

OTHER PUBLICATIONS

Yamane et al.–Japan J. Med. Sci. Biol., vol. 31 (1978) pp. 431–434.
Nicholson, K. G. et al.–J. Biol. Standardization vol. 7 (1979) pp. 123–136.
Murphy et al.–IVth Intern. Congr. Virol. (The Hague 1978).
Boudreault–Canad. J. Microbiol. vol. 25 (1979) pp. 279–284.
Rott et al.–J. Gen. Virol. vol. 44 (1979), pp. 471–477.
Oxford et al.–Nature vol. 273 (Jun. 9,1978) pp. 778–779.
Hay et al.–Int. Sym. Infl. Immun. Geneva 1977, Develop. Biol. Stand. vol. 39, pp. 15–24.
Cox et al.–Virology vol. 97 (1979) pp. 471–477.
Mahy et al.–Negative Strand Viruses and the Host Cell (1978) Academic Press–Article by Rott et al. pp. 653–662.

*Primary Examiner*—Sam Rosen
*Attorney, Agent, or Firm*—Janice E. Williams; Richard D. Foggio; Alan D. Lourie

[57] ABSTRACT

The invention relates to a novel influenza virus strain and to the influenza virus vaccine containing said strain.

The new strain, which is the CNCM I-062 strain, is prepared by recombination of the influenza A/PR/8/34 virus strain with the influenza A/Alaska/5/77 virus strain.

The vaccine is prepared by allowing the CNCM I-062 strain to grow in the allantoic cavity of fertile hen's eggs, harvesting and freeze-drying the yielded virus material.

The strain and the vaccine deriving therefrom are valuable for the immunization against influenza caused by influenza type A ($H_3N_2$) virus strains.

4 Claims, No Drawings

LIVE INFLUENZA VIRUS VACCINE AND THE PREPARATION THEREOF

The present invention relates to a novel attenuated influenza type A virus strain and to the live influenza vaccine for nasal administration containing it.

Up to now, different techniques have been employed for attenuating influenza virus: (a) recombination of a pathogenic variant with an antigenically distinct virus strain known to be attenuated for man; (b) serial passage at low temperature to derive a "cold" mutant and the transfer of this property to pathogenic strains by recombination; (c) use of a chemical mutagen to induce temperature sensitive (TS) mutants and the transfer of the TS property by recombination to pathogenic strains and (d) selection of inhibitor resistant mutants (Immunologic and Infectious Reactions in the Lung, edited by Charles H. Kirkpatrick and Herbert Y. Reynolds, Marcel Dekker Inc., New York and Basel, 1976, p.390, chapter entitled "Vaccines for Non-Bacterial Respiratory Disease" by R. M. Chanock).

Almost every year the serotype of the influenza type A virus strains spreading throughout the world appears to be somewhat different from the serotype of the previously observed strains. This antigenic modification creates particular problems for the immunization against influenza virus type A. For maximal efficacy, the vaccinal antigen indeed must be as close as possible to the antigen of the prevailing virus and, therefore, the attenuated live virus vaccines must be periodically adapted, in order to be effective against these new strains.

The present invention relates to the production of an influenza type A ($H_3N_2$ serotype) virus strain by recombination of the attenuated A/PR/8/34 influenza virus strain with a recently isolated pathogenic strain which is the influenza A/Alaska/5/77 virus strain.

By recombination of the attenuated A/PR/8/34 influenza virus strain (which has the $H_0N_1$ serotype and presents a high growth capacity) with the pathogenic influenza A/Alaska/5/77 virus strain (which has the $H_3N_2$ serotype), we have been able to isolate a novel attenuated influenza virus strain which has the $H_3N_2$ serotype. This novel strain named RIT 4199 presents a 67% (±3%) RNA/RNA hybridization rate with the A/PR/8/34 when determined by the method described by G. Florent & al. in Arch. Virol. 54, 19–28, 1977. The RIT 4199 strain is virtually non pathogenic; it is particularly well adapted for the production of a vaccine against the influenza A/Texas/1/77 virus strain and the like, more particularly for the production of a live vaccine administrable by nasal route.

The influenza A/Alaska/5/77 virus strain is a wild strain isolated from patients in Alaska and received from the WHO Collaborating Center for Influenza, Atlanta, Ga., USA at the fourth passage in SPAFAS eggs (from SPAFAS INC., Storrs, Connecticut, USA). Its serotype is identical to the one of the influenza A/Texas/1/77 prototype strain. The influenza A/Alaska/5/77 strain was deposited with the "Collection Nationale de Cultures de Microorganismes" (C.N.C.M.) of the "Institut Pasteur" in Paris under CNCM No. I-063.

The influenza RIT 4199 virus strain was deposited with the same collection under CNCM No. I-062.

Thus, the present invention relates to the novel influenza A virus CNCM I-062 strain, to the live influenza virus vaccine comprising an effective dose of the influenza A virus CNCM I-062 strain and a pharmaceutical diluent for nasal administration.

The influenza A virus CNCM I-062 strain is a recombinant obtained by mixing aliquots of both the A/PR/8/34 and A/Alaska/5/77 strains, allowing the mixture to stay a few hours at 4° C., inoculating the mixture in the allantoic cavity of fertile hen's eggs, incubating the inoculated eggs, harvesting the viral material and cloning it by limiting dilution passages.

For preparing a vaccine according to the invention, the recombinant influenza A virus CNCMI-062 strain is allowed to grow in fertile eggs, more particularly in the allantoic cavity of fertile hen's eggs, according to any technique known to the art for the production of vaccines, for a period of time sufficient to permit production of a large amount of said virus, harvesting the resulting virus material and, if desired, adding thereto a stabilizer, such as for instance peptone, sucrose and other ones known to the art, distributing the mixture into glass vials to contain either single or multiple doses of vaccine and freeze-drying the preparation. Preferably, an effective vaccine dosage unit contains at least $10^7 EID_{50}$ (50% egg infective dose) of virus.

The vaccine according to the invention is administered by nasal route, eventually after extemporaneous reconstitution by addition of either water or any other pharmaceutical diluent or composition known to the art for the preparation of nasal preparations such as drop or spray.

For assuring the best vaccinal answer, the vaccine may, if desired, be administered by inoculation of two successive dosage units at a one week interval.

The present invention is illustrated by the following examples wherein the indicated eggs are all originating from SPF flocks meeting the Specifications for the Production and Control of Avian Live Virus Vaccines established by the British Ministry of Agriculture, Fisheries and Food (1976). These examples should not be construed as limiting the scope of the invention.

EXAMPLE 1

A 0.5 ml aliquot of a reconstituted suspension of the lyophilized A/PR/8/34 influenza virus strain containing $10^{8.3} EID_{50}$ thereof per milliliter is mixed with a 0.5 ml aliquot of allantoic liquid of fertile hen's eggs containing $10^{8.1} EID_{50}$ of the CNCM I-063 influenza virus strain per milliliter and the mixture is maintained at 4° C. for a few hours.

The mixture is then inoculated into the allantoic cavity of fertile hen's eggs which are incubated at 35° C. for 20 hours.

The progeny of this mixed culture is harvested, diluted to 1/10 (v/v) and mixed with the same volume of anti A/PR/8/34 hen's serum diluted 1/100(v/v) and treated with kaolin. After one hour at 37° C., it is inoculated in the allantoic cavity of fertile hen's eggs which are then incubated for 24 hours at 35° C. Another passage is thereafter performed in the same conditions but for 48 hours.

The obtained virus is then cloned in the allantoic cavity of fertile hen's eggs by limiting dilution passages, a first passage being performed in the presence of treated and 1/100 (v/v) diluted anti A/PR/8/34 hen's serum, a second passage being performed without serum and two further passages being performed in the presence of normal guinea pig serum.

One so-isolated strain has been selected, characterized and assigned the RIT 4199 designation and deposited with the "Collection Nationale de Cultures de Microorganismes" (C.N.C.M.) of the "Institut Pasteur" in Paris under CNCM No. I-062.

EXAMPLE 2

Characterization of the influenza virus CNCM I-062 strain

The CNCM I-062 strain has been examined for its serotype and for its generic homology with the parent A/PR/8/34 strain expressed as the percentage of molecular hybridization between the virion RNA of the CNCM I-062 strain and the complementary RNA of the A/PR/8/34 strain, according to the method described by G. Florent & al. in Arch. of Virol. 54, 19–28, 1977.

The characteristics of the CNCM I-062 strain are given in the following Table I with the corresponding characteristics of the A/PR/8/34 and CNCM I-063 parent strains.

TABLE I

| Strain | Serotype | Percentage of hybridization |
|---|---|---|
| A/PR/8/34 | $H_0N_1$ | 100 |
| CNCM I-063 | $H_3N_2$ | 38 ($\pm$ 3%) |
| CNCM I-062 | $H_3N_2$ | 67 ($\pm$ 3%) |

By polyacrylamide gel electrophoresis identification of the doubled stranded RNA formed after hybridization according to the method described by A. J. Hay et al. in Int. Symp. on Infl. Immun. (II) Geneva 1977 Develop.Biol.Standard. 39, 15–24(S. Karger, Basel 1977), it has been determined that the CNCM I-062 strain has the genes corresponding to RNA's 1,3,5,7 and 8 of the A/PR/8/34 parent strain and the genes corresponding to RNA's 2,4 and 6 of the CNCM I-063 parent strain, the RNA's 4 and 6 coding for hemagglutinin and neuraminidase, respectively.

EXAMPLE 3

Vaccine preparation

Influenza virus CNCM I-062 strain obtained at the end of the last passage of example 1, is used as inoculum for the production of vaccine seed batch production.

An aliquot of said CNCM I-062 strain obtained at the end of example 1, is inoculated into the allantoic cavity of fertile hen's eggs which are then incubated at 35° C. for 2 to 3 days.

The allantoic fluids containing the CNCM I-062 strain are harvested, pooled and tested for sterility and innocuity and peptone is added thereto up to yielding a 5%(v/v) peptone concentration.

The virus suspension is distributed into 3 ml vials in order to obtain dosage units (at least $10^7 EID_{50}$) of influenza virus and freeze-dried. The vials are then tightly stoppered.

For administration, the vaccine is reconstituted extemporaneously by addition of 0.5 ml of a diluent which is, for instance distilled water, normal saline or aqueous solution of sucrose (5% w/v) and the reconstituted vaccine is administered into the nostrils.

EXAMPLE 4

Vaccination with one dosage unit of attenuated influenza virus vaccine, CNCM I-062 strain Material and methods Fourteen subjects from 23 to 43 year old (mean age: 30 years) having an HI antibody titre (i.e. determined by haemagglutination inhibition) equal to or inferior to 20, except one subject who had an HI titre of 40, were selected for the clinical trial. To each subject a dosage unit of vaccine containing $10^{7.3} EID_{50}$ of the CNCM I-062 strain obtained at the end of example 3 and reconstituted just before administration in 0.5 ml a sterile 5%(w/v) sucrose aqueous solution was administered by nasal route, each subject in supine position receiving 5 drops of vaccine in each nostril.

For the determination of seroconversion (which corresponds either to an HI antibody titre increase from $<10$ to $\geq 10$ or, when the prevaccination HI antibody titre is $\geq 10$ to a fourfold increase of the HI titre), blood samples were collected for the determination of HI antibody titre against the CNCM I-062 strain, between 2 and 3 months before vaccination (except case 31: 7 months before vaccination) and 21 days after vaccination.

For 6 subjects, nasal washings were also collected 2 and 3 days after vaccination.

Results

1. Clinical reactions

Eleven subjects had no symptoms and the remaining three had only mild rhinorrhea for two or three days.

2. Virus excretion

Nasal washings were collected on day 2 and day 3 in 6 subjects, i.e. No. 147, 156, 161, 186 and 190 who were seronegative before vaccination and No. 31 who had an HI titre of 40 before vaccination. The vaccine virus was not recovered from any subject either on day 2 or on day 3.

3. Serology

Table II shows the serum antibody titres determined by haemagglutination inhibition (HI) against the CNCM I-062 strain 21 days after vaccination versus the serum antibody titres determined by haemagglutination inhibition before vaccination.

TABLE II

| Serum antibody titres against the CNCM I-062 strain (expressed in HI units) | | |
|---|---|---|
| | HI units | |
| Subjects | before vaccination | after vaccination |
| 159 | $<10$ | $<10$ |
| 148 | $<10$ | $\leq 10$ |
| 156 | $<10$ | 10 |
| 172 | $<10$ | 10 |
| 190 | $<10$ | 10 |
| 189 | $<10$ | 10/20 |
| 147 | $<10$ | 20 |
| 171 | $<10$ | 20 |
| 186 | $<10$ | 20 |
| 161 | $<10$ | 40/80 |
| 220 | $<10$ | 80 |
| 200 | 10 | 320 |
| 157 | 20 | 40/80 |
| 31 | 40 | 160 |

It appears from Table II that, among the subjects having an HI antibody titre equal to or inferior to 20 before vaccination, 11 out of 13 (i.e. 85%) seroconverted and that the subject who had an HI antibody titre of 40 before vaccination also seroconverted. Thus, among the 14 subjects, 12 (i.e. 86%) seroconverted. The geometric mean titre for the sub-population with a prevaccinal titre equal to or inferior to 20 rose from 6 to 20. It can be concluded that the vaccine caused insignificant reactions, was not shed and elicited a satisfactory serum HI antibody response in most subjects.

EXAMPLE 5

Vaccination with two successive dosage units of attenuated influenza virus vaccine, CNCM I-062 strain

Material and methods

Fourteen subjects from 19 to 42 year old (mean age: 25 years) received, at a 7 day interval, two doses of influenza virus vaccine CNCM I-062 strain obtained at the end of example 3 and reconstituted in 0.5 ml of a sterile 5% (w/v) sucrose aqueous solution just before administration. The vaccine titre was $10^{7.3} EID_{50}$ and was administered by nasal instillation of 5 drops per nostril. The antibody titres determined by haemagglutination inhibition (HI) are indicated in Table III. Sera for selection of subjects had been collected three days before the first vaccine administration. The antibody titre of the vaccinated subjects was determined from blood samples collected 21 days after the first vaccine administration.

Results

1. Clinical reactions

The vaccinees were checked for eventual symptoms such as rhinorrhea, hoarseness, nasal stuffiness, sore throat, cough, nature of expectoration and headache. Among them, six (No. 167, 236, 240, 241, 242 and 245) had no symptoms at all. One (No. 243) had moderate rhinorrhea for two days. Another one (No. 234) reported mild cough which started on the vaccination day. One (No. 238) reported moderate rhinorrhea on days 3 and 4, moderate nasal stuffiness on days 6 and 7 and moderate cough on days 3 and 7. Subject No. 233 reported moderate headache for 7 days starting on day 0. Subject No. 235 reported mild to moderate headache from day 1 to day 6. Subject No. 244 reported four temperature rises (i.e. at least 37.5° C.) from day 3 to 6 in the evening, moderate nasal stuffiness from day 4 to 6, severe rhinorrhea from day 2 to 3, moderate to severe sore throat from day 2 to 7 and severe cough from day 4 to 7; he also complained of moderate to severe headache from day 2 to 6; however, he did not seroconvert after vaccination. Symptoms check lists were not available for No. 237 and 239. Since these subjects did not report to the investigator, one may suppose that they had no severe side effects.

Subjects who reported headache only can probably be excluded from those who had vaccine-related reactions.

2. Serology

The following Table III shows the individual results for serum antibody titres as determined by haemagglutination inhibition (HI) technique against strain I-062, 21 days post vaccination versus the serum antibody titres determined by haemagglutination inhibition before vaccination.

TABLE III

Serum antibody titres against the CNCM I-062 strain (expressed in HI units)

| | HI units | |
|---|---|---|
| Subject | before vaccination | after vaccination |
| 244 | <10 | <10 |
| 243 | <10 | 10 |
| 240 | <10 | 10 |
| 235 | <10 | 10 |
| 233 | <10 | 20 |
| 237 | <10 | 40 |
| 239 | <10 | 40 |
| 241 | <10 | 40 |
| 242 | <10 | 320 |
| 238 | <10 | ≧640 |
| 236 | <10 | 160 |
| 167 | 10 | 40 |
| 234 | 10 | 320 |
| 245 | 80 | 320 |

Among the 13 subjects having a prevaccination antibody titre equal to or inferior to 10, 12 (i.e. 92.3%) seroconverted and the subject who had a prevaccination HI titre of 80 (No. 245) also seroconverted. The geometric mean titre increased from 6 prior to vaccination to ≧44 three weeks after the first dose administration for the population with prevaccination HI titre ≦10 and from 7 to ≧51 for the whole population.

It appears from the trial that the vaccine produces only mild reactions that are clinically acceptable.

We claim:

1. The recombinant influenza virus CNCM I-062 strain.

2. A live influenza virus vaccine composition comprising an effective dose of the recombinant influenza virus CNCM I-062 strain and a pharmaceutical diluent for nasal administration.

3. A live influenza virus vaccine composition according to claim 2 wherein the effective dose is at least $10^7 EID_{50}$.

4. A process of producing a live influenza virus vaccine according to claim 2 which comprises allowing the recombinant influenza virus CNCM I-062 strain to grow in the allantoic cavity of embryonated chicken eggs for a period of time sufficient to permit production of a large amount of said virus, harvesting the resulting virus material and, if desired, adding thereto a stabilizer and freeze-drying the mixture.

* * * * *